United States Patent [19]

Cubbon et al.

[11] 4,233,462
[45] Nov. 11, 1980

[54] PEROXYGEN COMPOUNDS

[75] Inventors: Robert C. P. Cubbon, Kingsley; John E. Braid, Croft, Nr. Warrington; Alfred E. Oates, Luton; Ronald Preston, Eccleston, all of England

[73] Assignee: Laporte Chemicals Limited, England

[21] Appl. No.: 509,715

[22] Filed: Sep. 26, 1974

Related U.S. Application Data

[60] Continuation of Ser. No. 48,531, Jun. 22, 1970, abandoned, which is a division of Ser. No. 660,199, Aug. 14, 1967, Pat. No. 3,787,503.

[30] Foreign Application Priority Data

Aug. 16, 1966 [GB] United Kingdom ............... 36641/66

[51] Int. Cl.$^3$ .......................................... C07C 179/025
[52] U.S. Cl. ................... 568/564; 568/567; 568/563; 260/338
[58] Field of Search ............. 260/610 R, 610 SC, 338; 568/563, 564, 567

[56] References Cited

U.S. PATENT DOCUMENTS

| | | | |
|---|---|---|---|
| 3,047,406 | 7/1962 | Ferrari et al. | 260/610 R |
| 3,077,412 | 2/1963 | Higashiuchi | 260/610 R |
| 3,015,631 | 1/1962 | McCloskey | 260/610 R |
| 3,085,014 | 4/1963 | Renner | 260/610 R |
| 3,160,667 | 12/1964 | Higashiuchi et al. | 260/610 R |
| 3,308,163 | 3/1967 | McKellin | 260/610 R |
| 3,326,809 | 6/1967 | Mageli et al. | 260/610 R |
| 3,546,249 | 12/1970 | Gerritsen et al. | 260/338 |

FOREIGN PATENT DOCUMENTS

937166  9/1963  United Kingdom ............... 260/610 R

OTHER PUBLICATIONS

J. Org. Chem., 23: 1322–1326 (1958), Kharash.

Primary Examiner—Werren B. Lone
Attorney, Agent, or Firm—Jacobs & Jacobs

[57] ABSTRACT

The invention relates to novel ketone peroxides compositions containing them and processes for producing the peroxides and the compositions. The ketone peroxides are those with an alkoxy or hydroxy substituent in the $\alpha,\beta$- or $\gamma$-position. The compositions contain (1) the peroxides and (2) water which may be in admixture with a hydrophobic or hydrophilic solvent or (3) a hydrophobic solvent. The peroxides are produced by reacting the $\alpha,\beta$- or $\gamma$-alkoxy or hydroxy ketone with aqueous hydrogen peroxide and a source of hydrogen ions, for example a mineral acid.

22 Claims, No Drawings

PEROXYGEN COMPOUNDS

This is a continuation of application Ser. No. 48,531 filed June 22, 1970, now abandoned which is a division of U.S. application Ser. No. 660,199 filed Aug. 14, 1967 which is the copending application, now U.S. Pat. No. 3,787,503.

The invention provides as novel compounds, α-, β- or α-hydroxy, or α-, β-, or α-alkoxy, ketone hydroperoxides and compositions containing them. The invention also provides such novel compounds which, in particular are based on butanones or pentanones, and also such novel alkoxy compounds having alkoxy groups of 1, or from 2 to 4, carbon atoms. The invention particularly provides, as novel compounds:
3-methoxy pent-2-one hydroperoxide
4-methoxy 4-methyl pent-2-one hydroperoxide
5-methoxy pent-2-one hydroperoxide
3-ethoxy but-2-one hydroperoxide
4-ethoxy but-2-one hydroperoxide
5-ethoxy pent-2-one hydroperoxide
3-hydroxy but-2-one hydroperoxide
3-hydroxy 3-methyl but-2-one hydroperoxide
4-hydroxy 4-methyl pent-2-one hydroperoxide
4-hydroxy but-2-one hydroperoxide
4-hydroxy 3-methyl but-2-one hydroperoxide
5-hydroxy pent-2-one hydroperoxide
and compositions containing them. Preferred compositions according to the invention, contain the hydroperoxide together with unreacted ketone and, either, water, or water and an organic hydrophilic solvent, or an organic hydrophobic solvent which may contain a small quantity of water.

The invention also provides a process for the preparation of ketone hydroperoxide-containing compositions which comprises forming a reaction mixture consisting essentially of α, β or γ-hydroxy ketone, or a β-methoxy ketone, aqueous hydrogen peroxide and a source of not more than 1.75 gram atoms of hydrogen ion per gram-mole of ketone and maintaining the reaction mixture until at least some of the hydrogen hydrophobic solvent which may contain a small quantity of water.

The invention also provides a process for the preparation of ketone hydroperoxide-containing compositions which comprises forming a reaction mixture consisting essentially of α-, β- or γ-hydroxy ketone, or a β-methoxy ketone, aqueous hydrogen peroxide and a source of not more than 1.75 gram atoms of hydrogen ion per gram-mole of ketone and maintaining the reaction mixture until at least some of the hydrogen peroxide has been consumed. The invention also provides a modification of the above process wherein the ketone is an α-, or γ-methoxy ketone or is an α-, β-, or γ-alkoxy ketone wherein the alkoxy group is other than a methoxy group.

A composition prepared from diacetone alcohol by the above process exhibits a number of hydroperoxidic properties. Firstly it is decomposed by lead tetraacetate with evolution of oxygen. Secondly it is possible to estimate the diacetone alcohol hydroperoxide present by liberation of iodine from sodium iodide in glacial acetic acid in the presence of a trace of ferric chloride hexahydrate. Thirdly the diacetone alcohol hydroperoxide present reacts with acetone in the presence of anhydrous copper sulphate to give a water insoluble peroxide. The peroxide gave an available $O_2$ value of 1.8 by the above mentioned iodine evolution test in the presence of ferric chloride method but gave an Av.$O_2$ value of 21.2 by the method of estimation involving liberation of iodine from sodium iodide in hydrochloric acid which last-mentioned method is applicable to dialkyl peroxides and cyclic ketone peroxides. In the process provided by this invention hydroperoxides are formed by reaction of carbonyl groups with hydrogen peroxide and the hydroxy or, as the case may be, alkoxy groups do not enter into the reaction.

A comparison of the $^1H$ nuclear magnetic resonance spectrum of a diacetone alcohol hydroperoxide composition (Av.$O_2$=9.4%) with the spectrum of diacetone alcohol shows that the peroxide composition contains an appreciable proportion of unreacted diacetone alcohol:

| | Group | Chemical shift p.p.m. | Relative Intensities | Ratio of H atoms |
|---|---|---|---|---|
| Diacetone alcohol 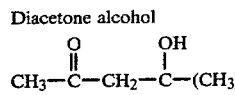 | $CH_2$ | 2.62 | 27 | 2 |
| | $CH_3$ | 2.18 | 42 | 3 |
| | $(CH_3)_2$ | 1.23 | 80 | 6 |
| | —OH | 3.97 | 12 | 1 |
| Diacetone alcohol hydroperoxide concentrate peaks assigned to diacetone alcohol | $CH_2$ | 2.68 | 15 | 2 |
| | $CH_3$ | 2.21 | 22 | 3 |
| | $(CH_3)_2$ | 1.28 | 39 | 6 |
| | OH | ~3.8 | | |
| peaks assigned to diacetone alcohol hydroperoxide 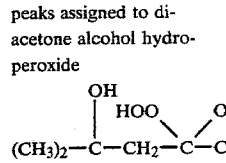 | $CH_2$ | 2.05 | 9.5 | 2 |
| | $CH_3$ | 1.56 | 16 | 3 |
| | $(CH_3)_2$ | 1.35 | 33 | 6 |
| | OH and OOH | ~3.8 | | |

The upfield shift of the $CH_2$ and $CH_3$ peaks on going from diacetone alcohol to diacetone alcohol hydroperoxide is of the order expected for reaction at the carbonyl group:

| Ketone | Ketone Peroxide | shift of peak due to CH$_2$ group p.p.m. |
|---|---|---|
| CH$_3$—C(=O)—CH$_2$—CH$_3$ | CH$_3$—C(HOO)(OOH)—CH$_2$—CH$_3$ | −0.75 |
| CH$_3$—C(=O)—CH$_2$—COC$_2$H$_5$ | CH$_3$—C(HOO)(OOH)—CH$_2$COC$_2$H$_5$ | −0.72 |
| (CH$_3$)$_2$—C(OH)—CH$_2$—C(=O)—CH$_3$ | (CH$_3$)$_2$—C(OH)—CH$_2$—C(HOO)(OOH)—CH$_3$ | −0.63 |

The peak due to hydroxyl and hydroperoxy groups in the peroxide composition spectrum is extremely broad. This is attributable to hydrogen bonding between the hydroperoxy groups and the alcohol groups.

Comparison of the intensities of the CH$_2$ peak of diacetone alcohol and the CH$_2$ peak of the peroxide in the composition spectrum shows that the composition contains 57% of diacetone alcohol. A 43% solution of the dihydroperoxide (AvO$_2$ 19.6) should have Av$_2$O$_2$ 8.6% which compares reasonably well with the value of AvO$_2$-9.4% actually found.

Thus the NMR spectrum is consistent with the proposed structure

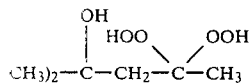

It establishes
1. that reaction takes place at the carbonyl group;
2. that the diacetone alcohol hydroperoxide composition contains about 50% of diacetone alcohol.

The reaction may be carried out by suspending the reaction mixture in an inert organic environment for example an inert organic liquid. The inert organic liquid may be a hydrophilic solvent such as mono- or polyalkylene glycols for example dipropylene glycol or hexylene glycol or other inert solvents known to have an affinity for water, or may be a hydrophobic solvent such as certain phthalate esters such as dimethyl phthalate thus providing compositions containing hydroperoxide together with unreacted ketone and, either, water and a hydrophilic organic solvent or a hydrophobic organic solvent which may contain a small quantity of water.

It is most essential in producing the novel compositions of our invention that the quantity of hydrogen ion used should not exceed 1.75 gram atoms per gram-mole of ketone. As the quantity of hydrogen ion is lowered non-hydroperoxidic materials may be produced but in a reduced quantity while an increasing quantity of our novel hydroperoxides is produced. When less than 0.1 gram-atoms of hydrogen ion is used per gram-mole of ketone our novel hydroperoxides are produced in optimum yield. Therefore advantageously less than 0.1 and preferably less than 0.05 gram-atoms of hydrogen ion per gram-mole of ketone is used. The minimum quantity of hydrogen ion which is desirably used is 0.0001 and preferably 0.00015 gram-atoms per gram-mole of ketone.

To obtain compositions containing the novel hydroperoxides in reasonable yields we prefer to use less than 1.5 and preferably less than 1.0 gram-atoms of hydrogen ion per gram-mole of ketone.

The source of hydrogen ion used in our invention is preferably a mineral acid, particularly a strong mineral acid such as sulphuric acid or hydrochloric acid. The acid may be introduced into the reaction medium while absorbed on an inert carrier. Alternatively a solid material having a content of hydrogen ion may be used for example a clay mineral such as those known by the Trade Name "Fulmont XX" or "Fulcat 14" or a suitable ion exchange resin.

Alternatively, or additionally, the hydrogen ion may be provided by organic acid present in situ in the aqueous hydrogen peroxide, for example as a consequence of manufacture or as a consequence of ionisation of the hydrogen peroxide itself. The acid may be introduced into the reaction mixture in any concentration which will not cause charring and, for example, it is desirable to introduce sulphuric acid into the reaction mixture as aqueous acid having a concentration below 50% w/w. The acid is preferably introduced as an aqueous solution of from 5 to 20% w/w.

The aqueous hydrogen peroxide used in this invention is advantageously of at least 65% w/w and preferably at least 80% w/w for instance desirably 85% w/w concentration except where it is desired to produce a novel composition, according to this invention, based on water. The hydrogen peroxide may be that produced by a cyclic process involving alternate reduction and oxidation of an organic intermediate for example a substituted anthraquinone. The aqueous hydrogen peroxide is preferably used so as to give a hydrogen peroxide:ketone molar ratio of from 1:1 to 3:1.

Where it is desired to manufacture one of the novel monomeric hydroperoxides in a high concentration the corresponding ketone is preferably reacted with aqueous hydrogen peroxide of high concentration advantageously at least 80% and preferably at least 85% w/w in the presence of from 0.0001 to 0.05 gram-equivalent of aqueous acid per gram-mole of ketone the hydrogen peroxide being present in an amount of not more than 2 gram-moles per gram-mole of ketone. Residual acid and unreacted hydrogen peroxide may be removed by washing the product, for example, with saturated ammonium sulphate solution where the acid used is sulphuric acid. Residual water may then be further reduced by contacting the product with anhydrous sodium sulphate or similar material. The resulting product contains 5 to 6% of water, 3 to 4% of hydrogen peroxide and in the region of 90% of a mixture of novel hydroperoxide and unreacted ketone. Substantially pure novel hydroperoxide may be prepared from such a composition by distillation at reduced pressure taking the safety precautions normally used when distilling peroxidic compounds.

The novel hydroperoxide of the invention may also be prepared in a high concentration by carrying out the process of the invention by forming the reaction mixture in an inert organic solvent in which both water and the novel ketone peroxides produced are insoluble, for example petroleum ether. Again, substantially pure hydroperoxide may be separated from the aqueous layer by known means for example by distillation. If the aqueous hydrogen peroxide used in the reaction is concentrated and if again, the source of hydrogen ion is less than 0.05 gram equivalents of aqueous acid per gram-mole of ketone the layer which separates from the organic medium on standing will comprise novel hydroperoxide, unreacted ketone and only a small proportion of water and hydrogen peroxide. Unreacted hydrogen peroxide, water and residual acid are removed by treating the peroxide layer as described above and substantially pure novel hydroperoxide may be obtained by removing residual unreacted ketone from the resulting composition.

The invention also provides several processes for the production of more dilute novel hydroperoxide containing compositions.

Such compositions, in the form of aqueous solutions, may be formed by carrying out the process of this invention in the presence of an aqueous medium. This is preferably obtained by using dilute hydrogen peroxide in the reaction mixture for example of 30% w/w concentration or less. The amount of water used is, however, desirably not substantially in excess of that which would be introduced by the use of 10% w/w concentration hydrogen peroxide in the reaction mixture.

A solution of the novel hydroperoxide in a hydrophilic organic solvent, for example dipropylene glycol, may be obtained by introducing the reaction mixture into an inert medium of the hydrophilic solvent. Alternatively a solution of the novel hydroperoxides in a hydrophobic organic solvent, for example dimethyl phthalate, may be obtained by carrying out the process of our invention in a hydrophobic solvent medium. When the novel peroxide produced is soluble in both water and the hydrophobic solvent it is advantageous to limit the quantity of water introduced with the reactants.

In practice, the process of the invention is suitably carried out by mixing the ketone, the source of hydrogen ion if not in the aqueous hydrogen peroxide, and the inert medium if used, and by adding to the mixture dropwise the aqueous hydrogen peroxide. The mixture is preferably maintained in agitation during the addition of the hydrogen peroxide. If a large proportion of acid is being used, for example more than 0.1 gram-equivalents per gram-mole of ketone, and if the reaction is being conducted in an aqueous medium, non-hydroperoxidic materials may form as a precipitate which is desirably filtered off. The reaction is advantageously carried out at a temperature of not more than 35° C. and preferably from 10° C. to 30° C. In some embodiments of the invention the reaction between the ketone and the hydrogen peroxide may not have gone to completion immediately after the addition of the hydrogen peroxide has been completed. Where the reaction is being carried out in an aqueous medium or in an organic medium which is a hydrophilic solvent for the novel hydroperoxide formed, the reaction mixture and the medium are advantageously allowed to stand for a period of time which varies with the reaction conditions used but which may, broadly, vary from 15 minutes to 16 hours. Where the reaction is being carried out in a hydrophobic medium or in a medium in which the novel peroxide formed is not soluble the reaction mixture and medium are, desirably, stirred for the requisite period of time.

In particularly advantageous embodiments this invention provides a process for the production of diacetone alcohol hydroperoxide-containing compositions which comprises forming a reaction mixture consisting solely of diacetone alcohol, aqueous hydrogen peroxide and from 0.0001 to 0.1 gram equivalents of a strong mineral acid per gram mole of ketone and maintaining the reaction mixture until at least some of the hydrogen peroxide has been consumed. Preferably the aqueous hydrogen peroxide is of at least 80% concentration by weight and the residual water is removed after substantial completion of the reaction thus producing a substantially pure diacetone alcohol hydroperoxide, diacetone alcohol composition from which diacetone alcohol hydroperoxide may be recovered. Alternatively the reaction mixture is suspended in a hydrophobic inert medium in which diacetone alcohol hydroperoxide is substantially insoluble and the aqueous phase containing diacetone alcohol hydroperoxide is separated and dried thus producing a substantially pure hydroperoxide ketone product. Alternatively the reaction mixture is suspended in an inert organic medium in which monomeric diacetone alcohol is soluble and water is either soluble or insoluble thus producing diacetone alcohol hydroperoxide containing compositions.

The invention will now be illustrated by means of the following examples of which Nos. 1–3, 7–28 and 38–42 are according to the invention, the remainder being inserted for comparative purposes.

EXAMPLES 1–6

25 g diacetone alcohol were mixed with 35 g of 30 w/w hydrogen peroxide and 150 ml of sulphuric acid. The mixture was left to stand for 65 hours at room temperature. Where a precipitate was produced it was filtered off.

| Example No. | Sulphuric acid strength of sulphuric acid. | g. atoms H+/ g. mole ketone | Diacetone alcohol hydro-peroxide in solution | g. washed & dried precipitate formed |
| --- | --- | --- | --- | --- |
| 1 | 0.5 N | 0.035 | YES | 1.6 |
| 2 | 1.0 N | 0.7 | YES | 7.5 |
| 3 | 2.0 N | 1.4 | YES | 7.8 |
| 4 | 3.0 N | 2.1 | NO | 10.0 |
| 5 | 4.0 N | 2.8 | NO | 13.0 |
| 6 | 5.0 N | 3.5 | NO | 13.0 |

The precipitate was proved by thin layer chromatography to be of a different compound from that remaining in solution and behaved identically on a thin layer chromatography plate to an authentic sample of mesityl oxide peroxide.

The comparison of Examples 1, 2 and 3 (according to the invention) and Examples 4, 5 and 6 (not according to the invention) demonstrates the criticality of the amount of acid used in the invention.

EXAMPLES 7–9

25 g diacetone alcohol, 11.1 g dimethylphthalate and 10 ml of aqueous sulphuric acid were stirred together and, while continuing the stirring, 17.3 g 86% w/w hydrogen peroxide were added over a period of 30 minutes the reaction temperature being maintained at not more than 30° C. After the addition of hydrogen peroxide has been completed the reaction mixture was stirred for a further 16 hours and was then washed with saturated ammonium sulphate solution and dried with anhydrous sodium sulphate.

| Example No. | sulphuric acid % w/w used | g. atoms H+/ g. mole ketone | Hydroperoxide Product Contained mesityl oxide peroxide | Av. O$_2$ content % w/w | residual H$_2$O$_2$ content % w/w |
|---|---|---|---|---|---|
| 7 | .7 | .046 | NO | 7.8 | 3.1 |
| 8 | 3 | .17 | YES | 5.9 | 0 |
| 9 | 9 | .87 | YES | 5.0 | 0 |

The presence of mesityl oxide peroxide dimer was established by comparing the product, by means of thin layer chromatography, with a sample of authentic mesityl oxide peroxide dimer. The different identity of the monomeric product from mesityl peroxide was established by the same means.

The above examples further illustrate the criticality of the amount of acid used.

EXAMPLE 10

78 g diacetone alcohol were stirred with 0.06 ml of 5% v/v sulphuric acid. (0.00016 g atoms H+ per g mole of diacetone alcohol) and 52 g 86% w/w hydrogen peroxide were added dropwise while continuing stirring, the temperature of the reaction mixture being maintained at 20° C. The reaction mixture was stirred for 16 hours at room temperature and the resulting solution was washed with saturated ammonium sulphate solution and dried with anhydrous sodium sulphate. The resulting product substantially comprised diacetone alcohol hydroperoxide and diacetone alcohol in about equal proportions. The product had an available oxygen content of 12.5%.

EXAMPLE 11

39 g of diacetone alcohol, 17 g of 40°–60° petroleum ether and 0.03 ml of sulphuric acid (5% by vol.) were stirred together in a beaker. 26 g of hydrogen peroxide (86% w/w) were then added dropwise and external cooling was applied so that the temperature of the reactants did not exceed 30° C. The reaction mixture was stirred at ambient temperature for a further 16 hours. When the stirring was stopped the reaction mixture separated into two phases. The lower diacetone alcohol peroxide layer was separated off, washed with saturated ammonium sulphate solution and dried with anhydrous sodium sulphate. The resulting diacetone alcohol hydroperoxide composition gave the following analysis:
Av.O$_2$ = 13.0% H$_2$O$_2$ = 3.5%

EXAMPLE 12

39 g of diacetone alcohol 17.0 g of dipropylene glycol and 1.6 g of Fulmont XX were reacted with 26.5 g of hydrogen peroxide (86% w/w) as in Example II. The Fulmont XX catalyst was then removed by filtration and the resulting diacetone alcohol hydroperoxide solution gave the following analysis:
Av.O$_2$ = 12.0%

Hydrogen peroxide = 0.6% by wt.

EXAMPLES 13–17

Acetol (4-hydroxy but-2-one) was prepared from bromo acetone by the method described in Organic Syntheses Collective Volume II edited by A. H. Blatt and published by John Wiley & Sons Inc.

37.0 g of acetol and 43.2 of dimethylphthalate were stirred in a beaker and 40 g of hydrogen peroxide (86% w/w) were added over a period of 10 minutes. The reaction mixture was cooled to maintain the temperature at 20° C. After 1½ hours 0.05 ml of sulphuric acid (5% by vol.) equivalent to 0.00018 g atoms H+/g mole ketone was added and the reaction mixture was stirred at ambient temperature for 16 hours. The reaction mixture was then washed with saturated ammonium sulphate solution and dried over anhydrous sodium sulphate. Analysis of the acetol hydroperoxide solution gave the following results:

Av.O$_2$ = 16.6% Hydrogen peroxide = 0.05% by wt.

This acetol hydroperoxide solution was very active in the cobalt catalysed gelation of Crystic 189 resin. 1% by weight of the resin of 1% white spirit/styrene solution of cobalt as the naphthenate was used.

| Wt. % of Acetol Hydroperoxide solution on the resin | Gel time min. | Cure time min. | Maximum temp, C. |
|---|---|---|---|
| 0.5 | 14 | 43 | 100 |
| 1.0 | 7.5 | 20 | 114 |
| 2.0 | 4.5 | 11 | 120 |
| 3.0 | 5 | 10 | 135 |
| 4.0 | 3 | 9 | 126 |

EXAMPLE 18

18.9 g of acetoin (3-Hydroxy but-2-one) 19.3 g dimethylphthalate and 0.02 ml of sulphuric acid (5% by vol.) were stirred in a beaker. 17.1 g of hydrogen peroxide (86% w/w) were then added dropwise over a period of 15 minutes. The reaction mixture was cooled to prevent the temperature exceeding 30° C. during the addition of the hydrogen peroxide. The reaction mixture was stirred at ambient temperature for 16 hours and was then washed with a saturated ammonium sulphate solution and dried over anhydrous sodium sulphate. The clear solution of acetoin hydroperoxide in dimethylphthalate gave the following analysis:

Av.O$_2$ = 5.6% Hydrogen peroxide = 3.0% by wt.

This solution readily catalysed the gelation of unsaturated polyesters in the presence of cobalt naphthenate. Data obtained for the gelation of Crystic 189 Resin is given in Table 5 using 1% white spirit/styrene solution of cobalt as the naphthenate.

| Wt. % of Acetoin Hydroperoxide solution on the resin | Gel time min. | Cure time min. | Maximum temp, °C. |
|---|---|---|---|
| 1 | 9.0 | 33 | 102 |
| 2 | 5.5 | 16 | 124 |
| 3 | 6.0 | 15 | 134 |
| 4 | 6.0 | 13 | 128 |

EXAMPLES 19–34

A mixture of 38.7 g of diacetone alcohol 28.8 g dimethylphthalate and 0.03 ml of 5% sulphuric acid was stirred in a beaker, 26.1 g hydrogen peroxide (87%) was then added dropwise over 30 minutes while external cooling was applied so that the temperature of the reactants did not exceed 30° C. The reaction mixture was left at ambient temperature overnight. The product was then washed with a saturated ammonium sulphate solution to remove unreacted hydrogen peroxide and the acid catalyst. This was followed by drying over sodium sulphate.

The resulting hydroperoxide in dimethylphthalate had the following analysis:

$Av.O_2 = 8.5\%$ $H_2O_2 = 3.2\%$ by wt. Dimethylphthalate $= 36.0\%$ by wt.

The following table shows that at this concentration the diacetone alcohol hydroperoxide was much more active than a typical methyl ethyl ketone composition of approximately the same concentration. This solution of the peroxide in dimethylphthalate was diluted with triethyl phosphate to give an available oxygen content of 4.2%. This had a similar activity to an MEKP solution having an available oxygen content of 13.8%. The solution of the diacetone alcohol peroxide was flame proof i.e. it could not be ignited by naked flame.

A sample of the same diacetone alcohol hydroperoxide-containing composition in dimethylphthalate was maintained at 40° C. for 14 days. Examination of the solution by thin layer chromatography showed that no new peroxidic species had been formed. The analytical results show that little decomposition had occurred during this test.

| Stability of diacetone alcohol hydroperoxide solution in dimethylphthalate | | | |
|---|---|---|---|
| | Analysis wt. % | | |
| | $Av.O_2$ | $H_2O_2$ | Free ketone |
| Original | 8.8 | 2.0 | 1.0 |
| After 14 days at 40° C. | 7.8 | 0.2 | 0.9 |

EXAMPLE 36

1-hydroxy 2-methyl but-3-one

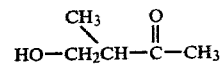

| | Gelation data for Crystic 189 Resin using a Peroxide and 1% addition of 1% solution white spirit/styrene of cobalt as the naphthenate by weight of the resin | | | | | | | | | | | | | | |
|---|---|---|---|---|---|---|---|---|---|---|---|---|---|---|---|
| Wt. % of ketone peroxide | Diacetone alcohol peroxide in dimethylphthalate | | | | | | | | 50% MEKP (RSG grade) | | | | 100% mesityl oxide peroxide dimer | | |
| | $Av.O_2 = 8.5\%$ | | | | $Av.O_2 = 4.2\%$ | | | | $Av.O_2 = 13.8\%$ | | | | | | |
| | Ex. No. | tg | tc | Tm°C. | Ex. No. | tg | tc | Tm°C. | Ex. No. | tg | tc | Tm°C. | Ex. No. | tg | tc | Tm°C. |
| 1 | 19 | 9 | 24 | 102 | 23 | 23 | 67 | 70 | 27 | 30 | 53 | 140 | 31 | >24 hrs. | — | — |
| 2 | 20 | 6.5 | 18 | 104 | 24 | 10 | 29 | 96 | 28 | 9.5 | 20 | 140 | 32 | ″ | — | — |
| 3 | 21 | 6 | 14 | 134 | 25 | 8.5 | 22 | 114 | 29 | 7.5 | 19 | 154 | 33 | ″ | — | — |
| 4 | 22 | 7 | 15 | 141 | 26 | 9 | 22 | 135 | 30 | 7 | 17 | 152 | 34 | ″ | — | — | tg = gel time (minutes)
tc = time to cure (minutes)
Tm = Maximum temperature (°C.)
— = No activity

EXAMPLE 35

154.6 g diacetone alcohol, 155 g dimethylphthalate and 0.13 ml of 5% aqueous sulphuric acid were stirred in a beaker. 104 g hydrogen peroxide (87%) were then added dropwise over 20 minutes. External cooling was applied so that the reaction temperature did not exceed 35° C. during the addition of hydrogen peroxide. The reactants were stirred at ambient temperature for 16 hours. The diacetone alcohol hydroperoxide solution was then washed with saturated ammonium sulphate solution. The hydroperoxide solution in dimethylphthalate was separated from the aqueous layer and dried with anhydrous sodium sulphate to give a clear solution. The solution gave the following analysis:

$Av.O_2 = 8.81\%$ $H_2O_2 = 2.0\%$ by wt.

The hazard properties of this solution were compared with 50% solution of methyl ethyl ketone peroxide in dimethylphthalate (RGS grade).

| Comparison of the hazard properties of 55% Diacetone Alcohol Hydroperoxide with MEKP (RGS grade) | | |
|---|---|---|
| Test | DAAP | MEKP (RGS grade) |
| Ignition time (disc test) | 80 sec. | 5–10 sec. |
| Pressure-time test | did not reach 300 psi. | 70 millisec. |
| Drop weight adiabatic compression test. | >120 kg.cm. | 10–15 kg.cm. |

10.2 g of this ketone, 8.7 g dimethylphthalate and 0.015 ml 5% aqueous sulphuric acid were stirred in a beaker, 8.44 g hydrogen peroxide (86%) were added dropwise over 15 minutes. The reaction temperature did not rise above 18° C. The reactants were stirred for 16 hours at ambient temperature and the resulting product was washed with saturated ammonium sulphate solution and dried over anhydrous sodium sulphate. The resulting hydroperoxidic solution in dimethylphthalate gave the following analysis:

$Av.O_2 = 10.3\%$ $H_2O_2 = 3.9\%$ by wt.

This solution readily cured Crystic 189 Resin in the presence of cobalt naphthenate and styrene.

EXAMPLE 37

2-hydroxy 2-methyl but-3-one

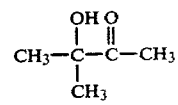

10.2 g of this ketone, 8.7 g dimethylphthalate and 0.015 ml 5% aqueous sulphuric acid were stirred in a beaker. 8.44 g hydrogen peroxide (86% w/w) was then added dropwise over 15 minutes. External cooling was applied to maintain the temperature below 30° C. The reactants were stirred at ambient temperature for 16 hours and then the product was washed with saturated ammonium sulphate and dried over sodium sulphate. The resulting hydroperoxidic solution gave the following analysis:

Av.O$_2$=7.3% H$_2$O$_2$=0.5% by wt.

This solution was also effective in curing Crystic 189 Resin in the presence of cobalt naphthenate and styrene.

EXAMPLE 38

4-methoxy 4-methyl pent-2-one

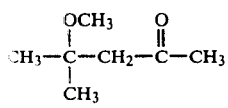

This methoxy ketone was prepared by the addition of methanol to mesityl oxide as described by N. B. Lorette J. Org. Chem., 23 937 (1958).

12.8 g methoxy ketone, 8.7 g dimethylphthalate and 0.015 ml 5% sulphuric acid were reacted with 8.44 g hydrogen peroxide (86%) as described in the previous examples.

The washed and dried product gave the following analysis:

Av.O$_2$=8.6% H$_2$O$_2$=1.8% by wt.

This hydroperoxidic solution was effective in the cobalt catalysed gelation of unsaturated polyesters.

What is claimed is:

1. A process for the preparation of a straight or branched chain ketone hydroperoxide of 4 to 6 carbon atoms substituted by alkoxy of 1 to 4 carbon atoms or hydroxy in the position α, β or γ to the ketone peroxide which consists essentially of treating at a temperature not exceeding 35° C. the corresponding ketone with aqueous hydrogen peroxide and a source of hydrogen ions providing 0.0001 to 1.75 gram atoms of hydrogen ion per gram mole of ketone.

2. A process as claimed in claim 1 wherein a source of not more than 1.5 gram atoms of hydrogen ion is used per gram mole of ketone.

3. A process as claimed in claim 1 wherein the reaction is carried out in an inert organic solvent.

4. A process as claimed in claim 1 wherein the reaction mixture is maintained at a temperature of from 10° C. to 35° C. until at least a portion of the hydrogen peroxide has been consumed.

5. A process as claimed in claim 1 wherein hydrochloric acid or sulphuric acid is used as the source of hydrogen ion.

6. A process as claimed in claim 5 wherein sulphuric acid is introduced into the reaction mixture as a solution having a concentration of between 5% and 50% by weight.

7. A process as claimed in claim 6 wherein the aqueous hydrogen peroxide is introduced into the reaction mixture as a solution having a concentration of between 10% and 87% by weight.

8. A process as claimed in claim 7 wherein the aqueous hydrogen peroxide is present in the reaction mixture in a hydrogen peroxide: ketone molar ratio of from 1:1 to 3:1.

9. A process as claimed in claim 1 wherein the ketone used is butanone or pentanone having one or more α-, or β-hydroxy groups.

10. A process as claimed in claim 9 wherein the ketone is 4-methyl-4-hydroxypentan-2-one, 3-hydroxybutan-2-one, 4-hydroxybutan-2-one, 4-hydroxy-3-methylbutan-2-one, or 3-hydroxy-3-methylbutan-2-one.

11. A process as claimed in claim 1 wherein the hydrogen peroxide:ketone molar ratio is from 1:1 to 3:1 and the reaction conditions are maintained until the hydrogen peroxide is substantially consumed.

12. A process as claimed in claim 11 wherein the hydrogen peroxide:ketone molar ratio is from 1:1 to 2:1.

13. A process as claimed in claim 12 wherein the hydrogen peroxide is introduced into the reaction mixture as a material having a concentration of at least 80% w/w.

14. A process as claimed in claim 13 wherein the mixture remaining after substantial consumption of the hydrogen peroxide is washed with saturated ammonium sulphate solution dried over anhydrous sodium sulphate and the product contains between 5% and 6% of water, between 3% and 4% of hydrogen peroxide and 90% of said hydroperoxide product and unreacted ketone.

15. A process as claimed in claim 11 wherein the reaction is carried out by suspending the reaction mixture in an inert organic solvent.

16. A process as claimed in claim 11 wherein the reaction mixture is suspended in an inert hydrophylic or hydrophobic organic solvent.

17. A process as claimed in claim 11 wherein the solvent is dipropylene glycol or dimethyl phthalate.

18. A process for preparing a peroxide composition, which comprises reacting diacetone alcohol with an aqueous solution of hydrogen peroxide wherein the molar ratio of the ketone alcohol to the hydrogen peroxide is equal to at least about 1:2, at a temperature in the range from about 10°-30° C., in the presence of a source of hydrogen ion providing 0.1 to 50 milligram equivalents of hydrogen ion per mol of diacetone alcohol, and subsequently reducing the residual acidity of the reaction mixture.

19. A process as claimed in claim 18 wherein the molar ratio of the ketone alcohol to the hydrogen peroxide is about 1:1.

20. A process as claimed in claim 18 wherein the reaction is carried out in an inert solvent.

21. A peroxidic composition, consisting essentially of peroxides derived from diacetone alcohol, prepared by a process according to claim 18.

22. A process as claimed in claim 18 wherein the source of hydrogen ions used is sulphuric acid.

* * * * *